US006306576B1

(12) United States Patent
Hazen et al.

(10) Patent No.: US 6,306,576 B1
(45) Date of Patent: Oct. 23, 2001

(54) DIAGNOSTIC METHODS FOR ASTHMA

(75) Inventors: Stan Hazen, Pepper Pike; Weijia Wu, Cleveland; David Schmitt, Lakewood, all of OH (US)

(73) Assignee: Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 09/253,380

(22) Filed: Feb. 19, 1999

(51) Int. Cl.[7] .................................................. C12Q 1/00
(52) U.S. Cl. .................................. 435/4; 435/7.1; 562/445
(58) Field of Search ........................ 435/7.1, 4; 562/445

(56) References Cited

U.S. PATENT DOCUMENTS 5,710,248 * 1/1998 Grose .................................... 530/327

FOREIGN PATENT DOCUMENTS

98/10294    3/1998 (WO) .

OTHER PUBLICATIONS

Smith–Gill, Research in Immunology, vol. 145: 67–70, 1994.*
The Merck Manual of Diagnosis and Therapy 16th Edition, 1992.*
"3–Bromotyrosine and 3,5–Dibromotyrosine Are Major Products of Protein Oxidation by Eosinophil Peroxidase: Potential Markers for Eosinophil–Dependent Tissue Injury in Vivo" by Wu, et al., *Biochemistry*, vol. 38, No. 12, 1999, pp. 3538–3548, Published on Web Mar. 5, 1999.
"3–Bormo–and 3,5–Dibromo–Tyrosine: Potential Markers for Eosinophil–Dependent Injury In Vivo" by Hazen, et al., Oxygen Society Annual Meeting, Washington, D.C., Nov. 1998, *Free Rad. Biol. Med.*, Supplement I, 25:S74 (#209).

* cited by examiner

*Primary Examiner*—Patrick J. Nolan
(74) *Attorney, Agent, or Firm*—Calfee, Halter & Griswold LLP

(57) ABSTRACT

Screening methods for asthma and analogous diseases in which activated eosinophils are found at the disease site are provided. The methods involve assaying for the presence of brominated tyrosine species in a bodily sample which has been obtained from a test subject. The brominated tyrosine species are either free in the sample or protein bound. In one embodiment, the assay involved measuring the amount of a brominated tyrosine species, particularly 3-bromotyrosine, 3,5-dibromotyrosine, or combinations thereof (referred to hereinafter collectively as the "diagnostic marker") in a bodily sample from the test subject. In another embodiment for determining the prognosis of asthma in a test subject, the concentration or content of the diagnostic marker is determined in bodily samples taken from the test subject over successive time intervals. The concentrations are compared to determine the prognosis of the asthma. In another embodiment of the invention for monitoring the response of the test subject to treatment with an anti-asthmatic drug, the concentration or content of the diagnostic marker is measured in bodily samples obtained from the test subject before and after such treatment. The present invention also relates to a diagnostic kit and to a diagnostic reagent for diagnosing asthma and analogous diseases which are associated with activated eosinophils.

43 Claims, 8 Drawing Sheets

Plasma Levels of 3-Bromotyrosine In an Acute Asthmatic Following Initiation of Steroid Therapy

DIAGNOSTIC METHODS FOR ASTHMA

BACKGROUND OF THE INVENTION

This invention relates to novel methods for diagnosing and screening for diseases which involve accumulation of activated eosinophils at the disease site. More particularly, this invention is directed to methods for diagnosing asthma.

Asthma is clinically defined as a reversible obstructive airway disease. Symptoms of asthma range from chronic cough and wheezing to severe difficulty in breathing and respiratory failure. Acute severe asthma (status asthmaticus) refers to an attack of increased severity that is unresponsive to routine therapy and that, if severe enough, can lead to death.

Chronic inflammation of the respiratory mucosa plays a fundamental role in the pathogenesis of asthma. Chronic inflammation causes increased mucus production which, along with asthmatic induced bronchospasms, leads to narrowing of the airways of the lung. The net result is a decrease in airway exchange in the lungs, decreased oxygenation of blood and tissues, and increased work of breathing.

The inflammation associated with asthma involves a number of different inflammatory cell types including eosinophils. Indeed, the earliest cellular hallmark of asthma is the eosinophil. Eosinophils and their granule constituents are present in blood, sputum and bronchial tissue of asthmatics early during asthma exacerbation.

At present there are no specific biochemical methods for diagnosing asthma or for monitoring the extent of ongoing inflammatory tissue injury in a subject diagnosed as having asthma. Furthermore, although there are numerous therapeutic agents which can be used for combating asthma, their use is limited by the lack of objective diagnostic biochemical assays with which to monitor their efficacy. Instead, therapy is initiated and adjusted based upon clinical exam, a patient's subjective response to therapy, and pulmonary function testing which does not directly assess the level of airway inflammation present.

Accordingly, it is desirable to have new methods for diagnosing asthma and other diseases which are characterized by the presence of activated eosinophils. New methods for monitoring the effect of treatment with anti-asthmatic drugs are also desirable. Methods which are simple and based upon a diagnostic marker are especially desirable.

SUMMARY OF THE INVENTION

In accordance with the present invention, screening methods for asthma and analogous diseases in which activated eosinophils are found at the disease site are provided. The methods comprise: assaying for the presence of brominated tyrosine species in a bodily sample which has been obtained from a test subject. As used herein, the term "test subject" refers to a mammal, preferably a human, suspected of having or known to have the disease. The brominated tyrosine species are either free in the sample or protein bound. Preferably, the assay is designed to detect the presence of 3-bromo-tyrosine, 3,5-dibromotyrsosine, or combinations thereof in the bodily sample. The methods are especially useful for diagnosing, determining the prognosis of, and monitoring asthma in a test subject. The methods of the present invention are also useful for detecting the presence of oxidative stress in a subject, for screening for analogous diseases involving activated eosinophils, and for monitoring the effectiveness of therapeutic interventions for asthma and analogous diseases involving activated eosinophils.

In one embodiment, the assay comprises measuring the amount of brominated tyrosine species, particularly 3-bromotyrosine, 3,5-dibromotyrosine, or combinations thereof (referred to hereinafter collectively as the "diagnostic marker") in a bodily sample from the test subject. Preferably, the concentration of the diagnostic marker in the bodily sample is determined and compared to the concentration of the diagnostic marker in corresponding bodily samples from normal subjects. Alternatively, the content of the diagnostic marker in the bodily sample is determined and compared to the content of the diagnostic marker in corresponding bodily samples from normal subjects.

In another embodiment for determining the prognosis of asthma in a test subject, the concentration or content of the diagnostic marker is determined in bodily samples taken from the test subject over successive time intervals. The concentrations are compared to determine the prognosis of the asthma. Alterations in the concentration or content correlate with the level of inflammatory tissue injury. An increase in concentration or content is indicative of increased inflammation.

In another embodiment of the invention for monitoring the response of the test subject to treatment with an anti-asthmatic drug, the concentration or content of the diagnostic marker is measured in bodily samples obtained from the test subject before and after such treatment. Preferably, the concentration or content of the diagnostic marker is measured in samples taken over successive time intervals following treatment. A decrease in the concentration or content of the markers following administration of the anti-asthmatic drug is indicative of decreased ongoing inflammatory tissue injury.

The present invention also relates to a diagnostic kit and to a diagnostic reagent for diagnosing asthma and analogous diseases which are associated with activated eosinophils. The diagnostic kit comprises an antibody reactive with a protein bound or peptide bound brominated tyrosine species. Preferably, the antibody is a monoclonal antibody reactive with proteins or peptides containing 3-bromotyrosine, 3,5-dibromotyrosine, or combinations thereof. The diagnostic reagent comprises a brominated tyrosine species selected from the group consisting of 3-bromotyrosine, 3,5-dibromotyrosine, a peptide or protein containing 3-bromotyrosine, and a peptide or protein containing 3,5-dibromotyrosine.

DETAILED DESCRIPTION OF THE INVENTION

Figure 1:
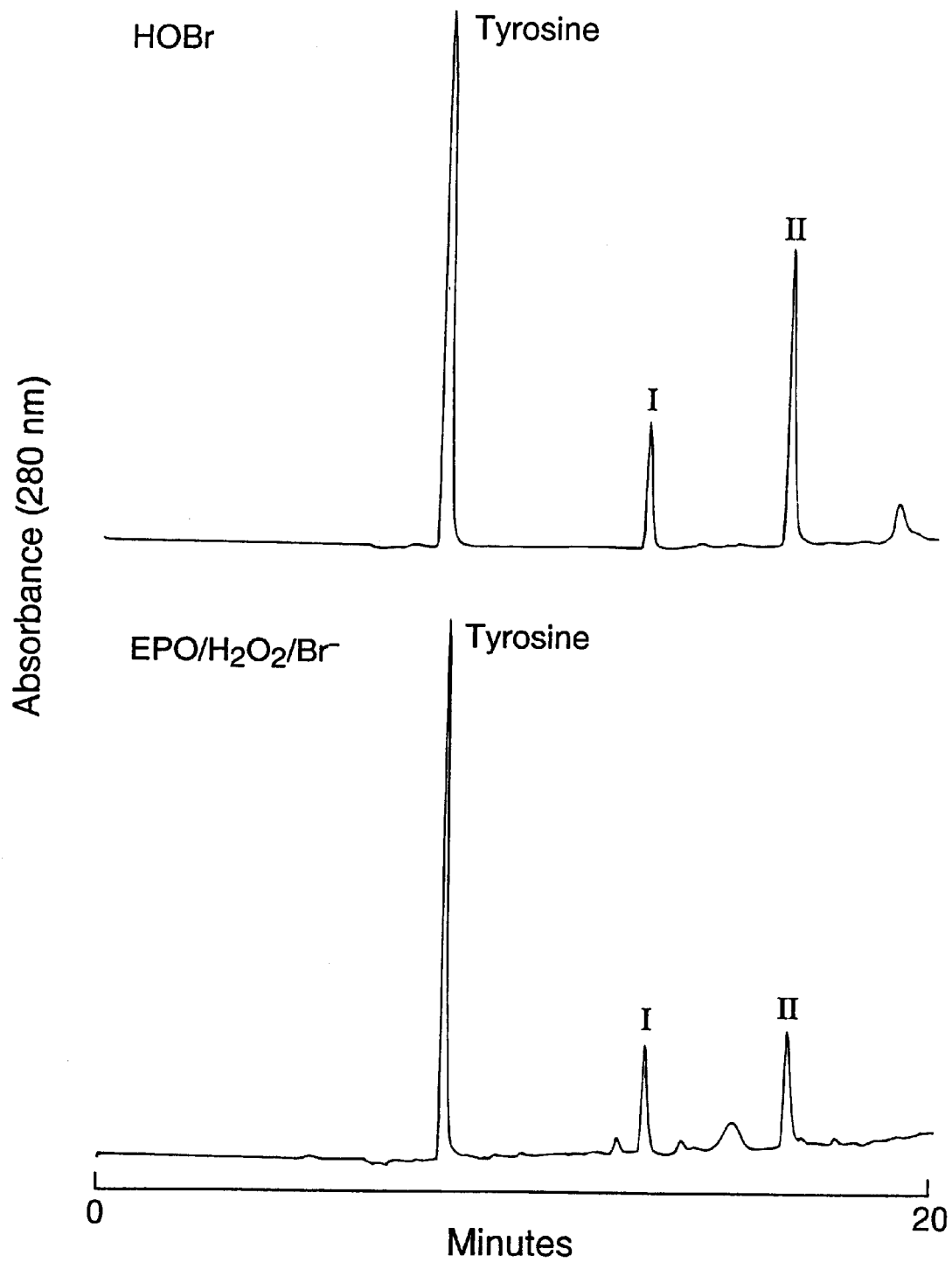
FIG. 1 is a graph showing reverse-phase HPLC separation of L-tyrosine oxidation products generated by hypobromous acid and eosinophil peroxidase.

Methods are provided for diagnosing diseases in which elevated levels of activated eosinophils are present at the disease site. The methods comprise assaying for the presence of brominated tyrosine species, preferably 3-bromotyrosine, 3,5-dibromotyrosine, or combinations thereof, in a bodily sample taken from a subject suspected of or known to have the disease, i.e., a test subject. The present invention also relates to kits and reagents for diagnosing diseases in which elevated levels of activated eosinophils are present at the disease site. Diseases associated with activated eosinophils are asthma, breast cancer, eosinophilic myocarditis, and eosinophilic cardiomyopathy. Other diseases associated with increased levels of activated eosinophils are described in Cecil's Textbook of Medicine, 17th Edition, Edited by James B. Wyngaarden and Lloyd H. Smith, Jr. (1985) W. B. Saunders Company, Philadelphia, Pa., pp 1012 and include, but are not limited to, allergies such as allergic rhinitis, atopic dermatitis, acute urticaria; and drug reactions; infectious diseases which involve invasive helminths; other infections such as acute coccidioidomycosis, afebrile tuberculosis, cat scratch disease, and chlamydial pneumonia of infancy; cutaneous diseases such as bullous pemphigoid, herpes gestationis, recurrent granulomatous dermatitis, and scabies; other pulmonary diseases such as transient pulmonary eosinophilic infiltrates (Löffler's syndrome), hypersensitivity pneumonia, allergic bronchopulmonary aspergillosis, tropical eosinophilia, and chronic eosinophilia pneumonia; connective tissue diseases in the polyarteritis group, e.g., allergic granulomatosis (Churg/Strauss type) and angitis with hepatitis B antigenemia, rheumatoid arthritis (severe), eosinophilic fascitis, and Sjögren's syndrome; neoplastic and myeloproliferative diseases such as solid tumors, lymphomas, T cell and acute lymphoblastic leukemia, hypereosinophilic syndrome, histiocytosis with cutaneous involvement, angiolymphoid hyperplasia (Kimura's disease); immunodeficiency diseases such as selective IgA deficiency, Swiss-type and sex-linked combined immunodeficiency, Nezelof syndrome, Wiskott-Aldrich syndrome, Hyper-IgE syndrome, and graft versus host reactions.

The methods are particularly useful for diagnosing diseases, such as asthma, in which bodily samples from a subject exhibiting active disease contain increased concentrations of free or protein-bound brominated tyrosine species including, but not limited to 3-bromotyrosine and 3,5-dibromotyrosine, relative to concentrations present in bodily samples from a subject lacking active disease.

I. Detecting the Presence of Brominated Tyrosine Species in Bodily Samples

The bodily samples used in the diagnostic method may be solid tissues such as, for example, a lung biopsy or a biopsy of any tissue where eosinophilic infiltration and activation is observed when a subject is afflicted with the respective disease; fluids and excretions such as for example, sputum, induced sputum, blood, serum, plasma, urine; ascites, stool, pericardial, pleural, cerebrospinal, or broncho-alveolar lavage; or cells containing metabolic products of activated eosinophils and phagocytes.

Preferably, the presence of brominated tyrosine species in the bodily sample is detected by measuring the amount of 3, bromotyrosine, 3,5, di-bromotyrosine or combinations thereof in the bodily sample. Depending upon the sample, the brominated tyrosine species are either free residues or bound to proteins obtained from the sample. In some cases, the amount or concentration of the brominated tyrosine species in the subject's sample is determined and normalized to the amount or concentration of another compound in the sample such as, for example, tyrosine, lysine, leucine, or any other amino acid which serves as an index of total protein content, total protein, albumin or creatinine, to provide the content of brominated tyrosine species in the sample.

Preferably, the diagnosis is made by comparing the concentration or content of the brominated tyrosine species in a sample obtained from the test subject to the concentration or content of the brominated tyrosine species in samples obtained from subjects lacking the disease, i.e., healthy or normal subjects. Alternatively, the concentration or content of the brominated tyrosine species in the sample is compared to the concentration or content in corresponding samples which were taken from the test subject for the purpose of determining baseline concentrations of the brominated tyrosine species. To establish baseline concentrations in an asthmatic subject, samples are taken at a time when the subject is not exhibiting asthma. To establish baseline concentrations in subjects with allergies, the samples, preferably, are taken during the time of year when allergens are lowest. For example, baseline measurements for subjects who suffer from typical pollen and grass allergies, preferably, are obtained during the winter.

A. Analytical Techniques for Measuring Protein Bound Brominated Tyrosine Species The preferred techniques for direct measurement of protein bound brominated tyrosine species from solid tissue samples or bodily fluids involves delipidation and desalting of the sample to provide a protein pellet which is then acid hydrolyzed to provide a solution containing amino acid residues. Tissue samples and bodily fluids containing proteins, are stored frozen until analysis. Preferably, the samples and fluids are stored under $N_2$ at $-80°$ C. and in the presence of a buffered solution containing metal chelators and antioxidants. Preferably, plasma or serum is obtained from whole blood samples prior to addition of buffer, metal chelators, antioxidants and freezing.

Thereafter, the samples are thawed, dried, and pulverized or homogenized to form a tissue powder or homogenate. The tissue powder is suspended in a phosphate buffer, supplemented with metal chelators, and antioxidants. Proteins are precipitated from the suspension preferably, by using a single phase-extraction mixture which is, preferably, comprised of $H_2O$:methanol-saturated diethyl ether. The protein fraction, which is free of lipid and salt, is recovered from the aqueous phase and then preferably dried under vacuum. Preferably, known amounts of stable-isotope-labeled 3-bromotyrosine and another labeled amino acid are added to the protein fraction to normalize values to protein content. In samples being prepared for stable isotope dilution mass spectrometric analysis, it is preferred that $^{13}C_6$-labeled 3-bromotyrosine and $^{13}C_6$-labeled tyrosine be added. The samples are then subjected to acid hydrolysis, preferably under halide-free conditions, such as in methane sulfonic acid.

It is preferable to partially purify the brominated tyrosine species, such as by passage over a mini solid-phase C18 extraction column followed by elution with a solvent such as a water:methanol mixture. The amount of brominated tyrosine residues, particularly 3-bromotyrosine and 3,5-dibromotyrosine, in the protein hydrolysate is then quantified by standard techniques such as reverse phase HPLC with electrochemical detection; reverse phase HPLC with coullometric array detection; reverse phase HPLC with pre- or post-column derivatization and fluorescence detection; reverse phase HPLC or capillary electrophoresis interfaced with an electrospray ionization mass spectrometer, or preferably, gas chromatography-mass spectrometry analysis following derivatization of the brominated and non-brominated L-tyrosine residues, preferably to their n-propyl per HFB derivatives. Mass spectrometric methods are preferable because of the ability to utilize isotopic dilution techniques for quantitation, as described in Heinecke, J. W., Hsu, F. F., Crowley, J. R., Hazen, S. L., Leeuwenburgh, C., Rasmussen, J. E. and Turk, J. "Detecting oxidative modification of biomolecules with isotope dilution mass spectrometry: Sensitive and quantitative assays for oxidized amino acids in proteins and tissues" In: Methods of Enzymology, Edited by Lester Packer, Vol. 300, pp. 124–145. Academic Press, Inc., San Diego. 1999. From these analytical techniques, the content of the brominated species in the sample is calcul d and, preferably, compared to values obtained when samples from normal subjects are analyzed in the same manner. The content of the brominated species in the sample are normalized to the protein content of the sample, preferably by determining the content of an amino acid such as tyrosine by isotope dilution mass spectrometry. Although not necessary, it is also possible to confirm the identity of the brominated L-tyrosine species using NMR.

In addition to the direct measurement techniques described above, protein-bound brominated L-tyrosine species, particularly 3-bromotyrosine and 3,5-dibromotyrosine, can be assayed using monoclonal antibodies that are reactive with such brominated tyrosine species. For example, anti-3 bromotyrosine antibodies may be made and labeled using standard procedures and then employed in immunoassays to detect the presence of protein-bound 3-bromotyrosine in the sample. Suitable immunoassays include, by way of example, radioimmunoassays, both solid and liquid phase, fluorescence-linked assays or enzyme-linked immunosorbent assays. Preferably, the immunoassays are also used to quantify the amount of the brominated tyrosine species that is present in the sample.

Monoclonal antibodies raised against brominated tyrosine species for use in such immunoassays are produced according to established procedures. Generally, the brominated tyrosine residue, which is known as a hapten, is first conjugated to a carrier protein and used to immunize a host animal. Preferably, the brominated tyrosine residue is inserted into synthetic peptides with different surrounding sequence and then coupled to carrier proteins. By rotating the sequence surrounding the brominated tyrosine species within the peptide coupled to the carrier, antibodies to only the brominated tyrosine species, regardless of the surrounding sequence context, are generated. Similar strategies have been successfully employed with a variety of other low molecular weight amino acid analogues.

Suitable host animals, include, but are not limited to, rabbits, mice, rats, goats, and guinea pigs. Various adjuvants may be used to increase the immunological response in the host animal. The adjuvant used depends, at least in part, on the host species. To increase the likelihood that monoclonal antibodies specific to the brominated tyrosine are produced, the peptide containing the brominated tyrosine species may be conjugated to a carrier protein which is present in the animal immunized. For example, guinea pig albumin is commonly used as a carrier for immunizations in guinea pigs. Such animals produce heterogenous populations of antibody molecules, which are referred to as polyclonal antibodies and which may be derived from the sera of the immunized animals.

Monoclonal antibodies, which are homogenous populations of an antibody that binds to a particular antigen, are obtained from continuous cells lines. Conventional techniques for producing monoclonal antibodies are the hybridoma technique of Kohler and Millstein (Nature 356:495–497 (1975)) and the human B-cell hybridoma technique of Kosbor et al (Immunology Today 4:72 (1983)). Such antibodies may be of any immunoglobulin class including IgG, IgM, IgE,IgA, IgD and any class thereof. Procedures for preparing antibodies against modified amino acids, such as for example, 3-nitrotyrosine are described in Ye, Y. Z., M. Strong, Z. Q. Huang, and J. S. Beckman. 1996. Antibodies that recognize nitrotyrosine. *Methods Enzymol.* 269:201–209.

B. Analytical Techniques for Measuring Free Brominated Tyrosine Residues

The preferred techniques for direct measurement of free brominated tyrosine species from solid tissue samples or bodily fluids involves removal of protein and lipids to provide a fluid extract containing free amino acid residues. The tissues and bodily fluids are stored, preferably in buffered, chelated and antioxidant-protected solutions, preferably at −80° C. as described above. The frozen tissue, and bodily fluids are then thawed, and extracted, preferably with a single phase mixture of methanol:diethylether:water as described above to remove protein. The fluid extract is preferably dried under vacuum, resuspended, preferably in a water:methanol mixture, supplemented with an internal standard. For stable isotope dilution mass spectrometry the internal standard is labeled with heavy isotope, preferably $^{13}C_6$. Thereafter, lipid is removed by extraction with organic solvents, preferably two-phase extraction with chloroform. The aqueous phase is then analyzed for brominated tyrosine species content as described above for the protein hydrolysate. For example, the sample is dried, passed over a mini solid-phase C18 extraction column, derivatized and analyzed by stable isotope dilution gas chromatography-mass spectrometry as above. Values of free brominated tyrosine species in tissues and fluids can be normalized to protein content, or an amino acid such as tyrosine as described above. When quantifying brominated tyrosine species in urine, differences in glomerular filtration rate are, preferably, accounted for by normalizing results to the urinary content of creatinine, which is determined by standard methods.

Advantageously, the present methods are either non-invasive or minimally invasive and provide an objective and quantifiable index of ongoing protein oxidative damage by reactive brominating species, such as at sites of activated eosinophils.

II. Diagnostic Kits and Reagents

Diagnostic kits and reagents which may be employed in assays to detect the presence of protein bound or free brominated tyrosine species in bodily samples of test subjects are provided. The diagnostic kit comprises an antibody, preferably a monoclonal antibody, which is used in an immunoassay to detect the presence of proteins or peptides modified by brominating oxidants, such as HOBr.

Preferably, the monoclonal antibody binds to or reacts with proteins containing 3 bromotyrosine, 3,5bromotyrosine, or combinations thereof. More preferably, the antibodies recognize proteins or peptides containing 3-bromotyrosine. Preferably, the diagnostic kit further comprises a synthetic peptide or protein containing bromotyrosine. Such peptide may be employed to generate a standard curve for quantification or as a competitor to demonstrate antibody specificity.

The diagnostic reagent is a brominated tyrosine species. Preferably, the diagnostic reagent is 3-bromotyrosine, 3,5-dibromotyrosine, a synthetic peptide containing 3-bromotyrosine, or a synthetic peptide containing 3,5-dibromotyrosine. For use in GC/MS it is preferred that the bromotyrosine species be multiply labeled with a heavy isotope such as $^2H$, $^{13}C$, and $^{15}N$ or, preferably, $^{13}C_6$.

III. Brominated Tyrosine Species as Specific and Stable Markers for Activated Eosinophils Activated eosinophils are found in the airways of asthmatic individuals. Activated eosinophils express and secrete eosinophil peroxidase (EPO). Increased levels of EPO and other markers of eosinophil activation are present in the airways of asthmatic individuals even in the earliest detectable stages of the disease, and the content of EPO in plasma and the airways correlate with the level of disease activity and the response to therapy.

EPO is a unique heme protein which selectively utilizes Br$^-$ (bromide) as substrate under physiological concentrations of halides (100 mM Cl$^-$ and 20–100 $\mu$M Br$^-$) to form the potent bactericidal, viricidal and cytotoxic oxidant HOBr (hypobromous acid).

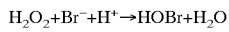

$$H_2O_2 + Br^- + H^+ \rightarrow HOBr + H_2O$$

Br$^-$ is ubiquitous in humans, and is present in virtually all biological fluids.

Unfortunately, HOBr, and most other oxidation products which are known to be generated by EPO, are either non-specific and/or decompose shortly after formation. Accordingly, the oxidation products which are known to be generated by EPO are not considered to be useful diagnostic markers for diseases associated with activated eosinophils.

In accordance with the present invention, it was found that brominated tyrosine residues, particularly, 3-bromotyrosine and 3,5-dibromotyrosine, are major oxidation products formed upon exposure of L-tyrosine to either the oxidant HOBr or to a system comprised of EPO, $H_2O_2$ and physiological concentrations of Br$^-$. It was also shown that HOBr can react with primary amines to form N-bromo amines, which can also act as brominating intermediates for 3-bromotyrosine and 3,5-dibromotyrosine formation at neutral pH and in near stoichiometric yield. Activated eosinophils were shown to employ EPO to brominate the aromatic ring of tyrosine residues on proteins forming 3-bromotyrosine and 3,5-dibromotyrosine. Collectively, these results suggest that tyrosine is an endogenous trap of reactive brominating species In accordance with the present invention, 3-Bromotyrosine was detected in human bronchoalveolar lavage from individuals with asthma compared to non-asthmatics; in bronchoalveolar lavage of asthmatic individuals exposed to an allergen, but not in non-asthmatic individuals similarly exposed, and in urine of an asthmatic, but not a non-asthmatic individual. It was also determined that 3-bromotyrosine levels in plasma from an asthmatic subject decrease following therapy. Collectively, these results demonstrate that brominated tyrosine analogs are formed in vivo. Moreover, these results indicate that brominated products such as 3-bromo-tyrosine and 3,5-di-bromo-tyrosine are useful diagnostic markers for diagnosing asthma and monitoring the efficacy of specific interventions.

METHODS

General Procedures. HOBr free of Br$^-$ and bromate was prepared from liquid bromine as described in Wajon, J. E. and Morris, J. C. (1980) in Bromination Chemistry.

Oxidation of free L-tyrosine and protein-bound tyrosyl residues. Reactions were initiated by addition of oxidant ($H_2O_2$, HOBr, N-bromo or N,N-dibromo amine) and performed in sodium phosphate buffer (pH 7.0) at 37° C. for 60 min. Proteins oxidized in vitro were prepared for analysis by first precipitating and desalting them in a single-phase extraction mixture comprised of $H_2O$:methanol:$H_2O$-saturated diethyl ether (1:3:7,v:v:v) as described in Hazen, S. L., Hsu, F. F., Gaut, J. P., Crowler, J. R. and Heinecke, J. W. "Modification of Proteins and Lipids by Myeloperoxidase-Derived Oxidants" In: Methods of Enzymology, Edited by Lester Packer, Vol. 300, pp. 88–106. Academic Press, Inc., San Diego. 1999., followed by acid hydrolysis in methane sulfonic acid.

Protein hydrolysis. Proteins were subsequently hydrolyzed under halide-free conditions by incubating the desalted protein pellet with 4 N methane sulfonic acid (0.5 ml) supplemented with 1% phenol for 24 h at 100° C. Prior to initiating hydrolysis, acid mixtures were degassed under vacuurr and then sealed under a blanket of argon.

Reverse phase HPLC quantification of L-tyrosine oxidation products. Quantitative determination of 3-bromotyrosine and 3,5-dibromotyrosine production from free L-tyrosine was performed utilizing reverse-phase HPLC with a C18 column (Beckman Ultrasphere, 5 $\mu$m resin, 4.6×250 mm) equilibrated with solvent A (0.1% trifluoroacetic acid, pH 2.5). L-tyrosine and its oxidation products were eluted at a flow rate of 1 ml/min with a linear gradient generated with solvent B (0.1% trifluoroacetic acid in methanol, pH 2.5) as follows: 0% solvent B for 5 min; 0–100% solvent B over 30 min; 100% solvent B for 10 min. 3-Bromotyrosine and 3,5-dibromotyrosine were monitored on a diode array detector and quantified at 280 nm employing a standard curve constructed with authentic synthetic standards.

3-Bromotyrosine and 3,5-dibromotyrosine in protein hydrolysates was quantified by reverse phase HPLC with electrochemical (coulometric) detection on an ESA (Cambridge, Mass.) CoulArray HPLC instrument equipped with 4 electrochemical cells (channels) utilizing platinum electrodes arranged in series and set to increasing specified potentials: channel 1 (320 mV); channel (440 mV); channel 3 (540 mV); and channel 4 (620 mV). Amino acid hydrolysates (50 $\mu$l) were injected onto a Projel TSK ODS-80 TM column (5 $\mu$m, 4.6×250 mm) equilibrated with mobile phase A (15 mM lithium phosphate, 3 mg/L lithium dodecyl sulfate, pH 3.2). Products were eluted at a flow rate of 1 ml/min with a nonlinear gradient generated with mobile phase B (50% methanol, 15 mM lithium phosphate, 3 mg/L lithium dodecyl sulfate, pH 3.2) as follows: isocratic elution at 0% mobile phase B for 10 min, 0–15% mobile phase B over 10 min, isocratic elution at 15% mobile phase B for 10 min, 15–20% mobile phase B over 10 min, isocratic elution at 20% mobile phase B for 10 min, 20–100% mobile phase B over 20 min, isocratic elution at 100% mobile phase B for 20 min. Peak identity was established by demonstrating the appropriate retention time, redox potential, ratio of integrated currents in adjacent channels, and by the method of standard additions for each analyte. L-Tyrosine, 3-bromotyrosine, and 3,5-dibromotyrosine standards (1–100 pmol each on-column) were also dissolved together and used to generate an external calibration curve.

Gas Chromatography Mass Spectrometric (GC/MS) Analysis. L-Tyrosine, 3-bromotyrosine and 3,5-dibromotyrosine generated by phagocytes and human tissues were quantified by stable isotope dilution GC/MS in the negative-ion chemical ionization mode. n-Propyl, per heptafluorobutyryl (HFB) derivatives of amino acids were prepared by standard methods and analyzed on a Perkin Elmer TurboMass mass spectrometer equipped with chemical ionization probe. Chromatographic separations were performed on a 20 m PE-5MS column (0.18 mm i.d., 0.18 μm film; Perkin Elmer), and mass spectra were acquired in the negative-ion mode. The column was run with the following temperature gradient: 150° C. to 250° C. at 20° C./min. The injector, transfer line and source temperatures were set at 250° C., 250° C. and 130° C., respectively. 3-Bromotyrosine was monitored as its n-propyl per HFB derivative using two structurally informative fragment ions, m/z 573 (M—HF)$^-$ and m/z 445 (M—$CF_3CF_2CHO$)$^-$ and their corresponding isotopically labeled [$^{13}C_6$] internal standard ions at m/z 579 and 451, respectively. 3,5-Dibromotyrosine was monitored as its n-propyl per HFB derivative at m/z 651 (M—HF)$^-$ and m/z 509 (M—$CF_3CF_2CONH$)$^-$ and their corresponding isotopically labeled [$^{13}C_6$] internal standard ions at m/z 657 and 516, respectively. L-Tyrosine was monitored as its n-propyl-per-HFB derivative using the base peak at m/z 417 ($M^{\bullet-}$—HFB), another major ion at m/z 595 ($M^{\bullet-}$—HF), and their corresponding isotopically labeled internal standard ions at m/z 423 and 601, respectively. The ratio of ion currents of the two characteristic ions of each compound and its corresponding internal standard were monitored in all analyses to ensure that interfering ions were not co-eluting with the analyte.

Instrumentation. Electrospray ionization mass spectrometry (ESI/MS) was performed on a Quatro II Triple Quadruple Mass Spectrometer (Micromass, Inc.) interfaced with an HP 1100 HPLC (Hewlett Packard). L-Tyrosine oxidation products were resolved on an Ultrasphere C18 column (Beckman, 5 μm, 4.6×250 mm) at a flow rate of 1 ml/min and a linear gradient between $H_2O$ (+0.3% formic acid) and methanol (+0.3% formic acid) over 30 min. Column eluent was split (970 μl/min to UV detector and 30 μl/min to mass detector) and analyzed by the mass spectrometer in the positive-ion mode with a cone potential of 23 eV. Gas chromatography-mass spectrometry (GC-MS) analysis of L-tyrosine oxidation products was performed following derivatization to their n-propyl per HFB derivatives on a Perkin Elmer TurboMass mass spectrometer equipped with chemical ionization probe. Chromatographic separations were performed on a 20 m PE-5MS column (0.18 mm i.d., 0.18 μm film; Perkin Elmer), and mass spectra were acquired in the negative-ion mode.

NMR studies were performed at 25° C. in $D_2O/H_2O$ (1:9, v/v) with a Varian Unity-Plus 500 spectrometer (4.99.843 MHz for $^1H$). $^1H$ chemical shifts were referenced to external sodium 3-(trimethylsilyl)-propionate-2,2,3,3,$d_4$ in $D_2O$. A Nalorac indirect detection probe was employed for $^1H$ and $^1H$, $^{15}N$ 2-dimensional NMR studies. The intense HOD signal was attenuated by transmitter pre-irradiation, and digital signal processing was employed to suppress phase distortions for $^1H$ spectra. $^{15}N$ NMR chemical shifts of L-tyrosine and its oxidation products were established through, heteronuclear multiple bond correlation spectroscopy experiments.

RESULTS

Reverse Phase HPLC Identification of Major L-tyrosine Oxidation Products of Eosinophil Peroxidase L-Tyrosine was incubated with eosinophil peroxidase, $H_2O_2$, and NaBr in sodium phosphate buffer, pH 7.4 at 37° C. for 60 min. In addition, L-Tyrosine (2 mM) was incubated with HOBr (2 mM) in sodium phosphate buffer (50 mM, pH 7.4) at 37° C. for 60 min. Products were subsequently analyzed by reverse phase HPLC as described above. As shown in FIG. 1, both HOBr and the enzymatic system generated two new major oxidation products with distinct retention times (designated Peaks I and II). Use of heat killed eosinophil peroxidase, or omission of either co-substrate ($H_2O_2$, or Br$^-$) resulted in no detectable production of the oxidation products by the enzymatic system. The reaction products formed were stable to treatment with acid, prolonged incubation at 37° C. with $H_2O_2$, and addition of a molar excess of either reducing agents or nucleophilic scavengers. These results strongly suggested that the products in Peaks I and II were not N-bromo amines.

Structural Identification of 3-bromotyrosine and 3,5-dibromotyrosine as Major Products of L-tyrosine Oxidation by Eosinophil Peroxidase-generated Reactive Brominating Species.

Figure 2:
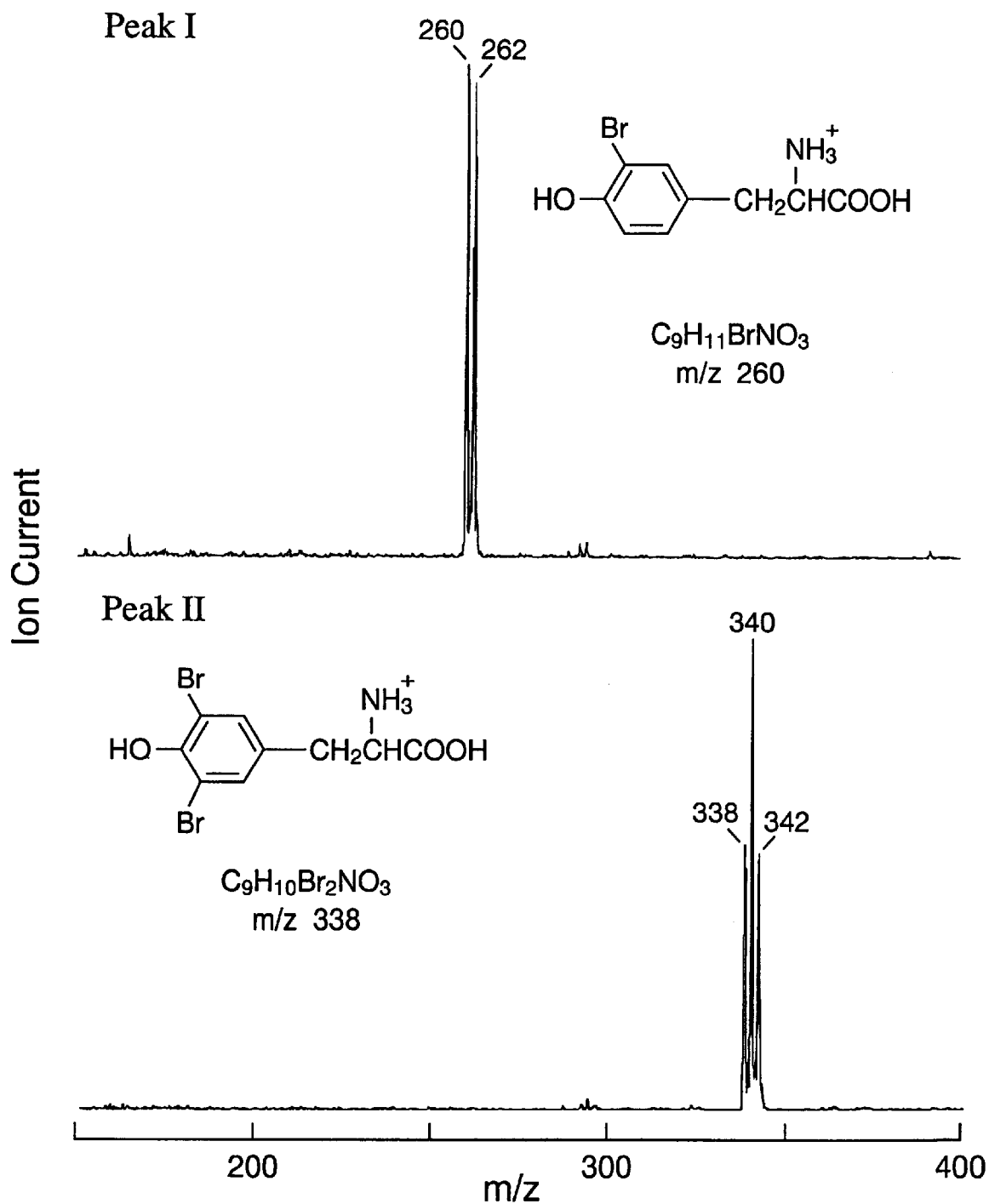
FIG. 2 is a graph depicting the positive-ion electrospray mass spectra of 3-bromotyrosine and 3,5-dibromotyrosine generated by the a system composed of eosinophil peroxidase, $H_2O_2$, and bromide.

To characterize the structures of the L-tyrosine oxidation products generated by the EPO-$H_2O_2$—Br$^-$ system, LC-MS analysis was performed. The positive ion mass spectrum of Peak I was consistent with a monobrominated derivative of tyrosine (FIG. 2, upper panel) and contained a single major compound possessing a mass-to-charge ratio (m/z) of 260 (M+H)$^+$. The mass spectrum also demonstrated the isotopic cluster expected for a mono-brominated compound (1:1, M:M+2), with ions at m/z 260 ([M+H]$^+$ for $^{79}$Br-containing isotopomer) and m/z 262 ([M+H]$^+$ for $^{81}$Br-containing isotopomer). These results, combined with the chemical stability of the product to acid, peroxide, reductants and nucleophilc compounds, suggested that Peak I was the stable ring-brominated product, 3-bromotyrosine (FIG. 2, upper panel inset). The positive ion mass spectrum of Peak II (FIG. 2, lower panel) was consistent with a dibrominated derivative of L-tyrosine and contained a single component with m/z 338 (M+H)$^+$. The mass spectrum demonstrated the isotopic cluster (1:2:1, M:M+2:M+4) expected for a dibrominated derivative of tyrosine, with ions at m/z 338 ([M+H])$^+$ for $^{79}Br_2$-containing isotopomer), m/z 340 ([M+H]$^+$ for $^{79}Br^{81}$Br-containing isotopomer) and m/z 342 ([M+H]$^+$ for $^{81}Br_2$-containing isotopomer). These results, combined with the chemical stability of the compound, suggested that Peak II was the stable ring-brominated product, 3,5-dibromotyrosine.

GC-MS analysis of the L-tyrosine oxidation products generated by the EPO-$H_2O_2$—Br$^-$ system (Peaks I and II) were also consistent with their structural assignment as 3-bromotyrosine and 3,5-dibromotyrosine, respectively. The negative-ion mass spectrum of the n-propyl per heptafluorobutyryl derivative of the product in Peak I demonstrated the anticipated molecular anion (M)$^{\bullet-}$ at m/z 593. Major ions observed in the mass spectrum and which also demonstrated the isotopic pattern of a mono-brominated species were observed at m/z 573 (M—HF)-, m/z 553 (M—2HF)$^-$, and m/z 445 (M—$CF_3CF_2CHO$)$^-$ (data not shown). Likewise, the negative-ion mass spectrum of the n-propyl per-heptafluorobutyryl derivative of Peak II was consistent with the structural assignment as 3,5-dibromotyrosine. Major ions observed in the mass spectrum and which demonstrated the isotopic pattern of a di-brominated species included m/z 671 (M)$^{\bullet-}$, m/z 651 (M—HF)$^-$, m/z 524 (M—CF$_3$CF$_2$CO)$^-$, and m/z 509 (M—CF$_3$CF$_2$CONH)$^-$.

Figure 3:
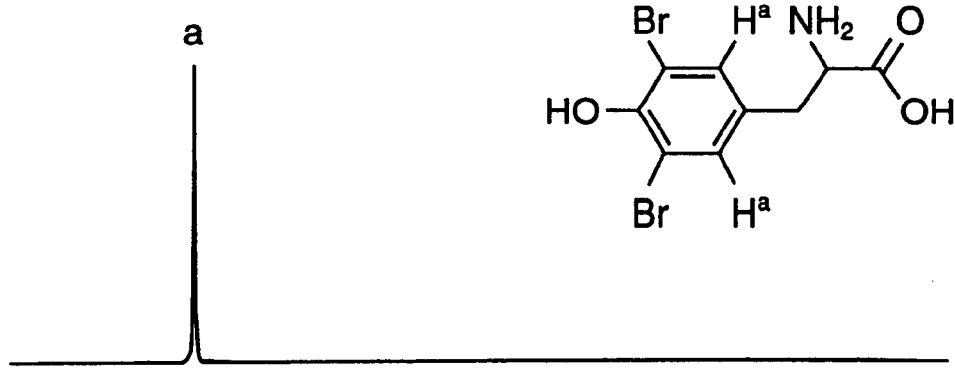
FIG. 3 is a graph showing the aromatic region of the $^1H$ NMR spectra of L-tyrosine, 3-bromotyrosine and 3,5-dibromotyrosine.
Figure 3:
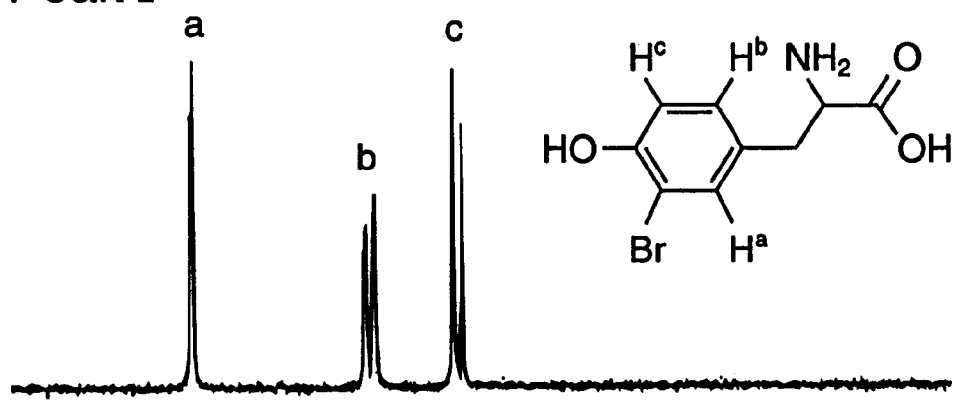
Figure 3:
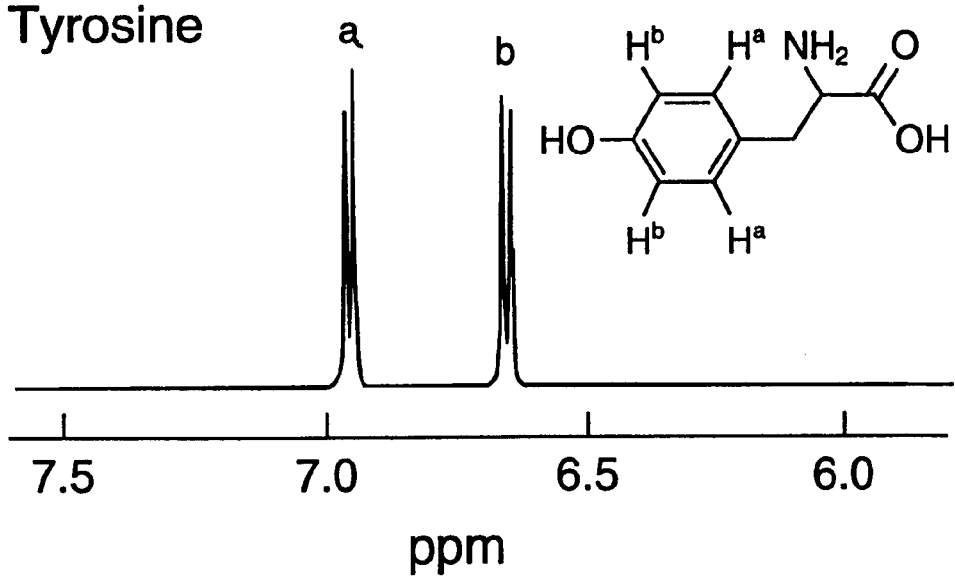

Multi-nuclear ($^1$H and $^{15}$N) NMR spectroscopy was employed to identify the precise location of Br attachment to the aromatic amino acid. $^{15}$N-labeled L-tyrosine was employed as starting material for oxidation by the EPO system since the $^{15}$N resonance could serve as a non-perturbing and sensitive probe into the immediate chemical environment at the α-amino nitrogen atom (where N-bromo amines might be formed) and concomitant examination of the aromatic region of the $^1$H NMR spectra to identify any stable ring-brominated adducts would also be feasible. $^1$H and $^{15}$N NMR analysis of L-[$^{15}$N] tyrosine and its EPO-H$_2$O$_2$—Br$^-$ oxidation products (Peaks I and II) confirmed the identity of these products as 3-bromotyrosine and 3,5-dibromotyrosine, respectively. The chemical shifts, integrated areas, and coupling constants of the resonances in the $^1$H NMR spectra were all consistent with formation of the stable ring-brominated adducts (FIG. 3). Proton assignments on the aromatic ring were further confirmed by observing allylic coupling between the benzylic protons and the ortho aromatic protons (positions 2 and 6) in both brominated species. Moreover, analysis of L[$^{15}$N]tyrosine and the EPO oxidation products by heteronuclear ($^1$H—$^{15}$N) multiple bond correlation spectroscopy demonstrated identical chemical shifts of the $^{15}$N resonances of the parent and oxidized amino acids, confirming that they did not represent N-bromo and N,N-dibromo amines (data not shown). Taken together, these results establish that the major tyrosine oxidation products generated by the EPO-H$_2$O$_2$—Br system are 3-bromotyrosine and 3,5-dibromotyrosine.

N-bromo Amines Mediate L-tyrosine Ring-bromination at Physiological pH.

L-tyrosine was incubated with either HOBr/OBr$^-$, N-bromo taurine, N,N-dibromo taurine or HOBr/OBr$^-$ in the presence of excess Br to enhance the equilibrium content of Br$_2$ in the mixture, and the levels of 3-bromotyrosine and 3,5-dibromotyrosine formed determined The results indicated that ring-brominated tyrosine species were readily produced following addition of all reactive brominating species. In particular, N-bromo amines formed the stable C-Br tyrosine adducts in almost quantitative yield. Further work showed that L-tyrosine ring bromination occurred at a pH ranging from 5 to 8. Interestingly, 3,5-dibromotyrosine was formed in particularly high yield at physiological pH resulting in the near quantitative formation of C-Br bonds (with respect to moles of reactive halogen consumed) at pH 7.4. Further work also showed that each mole of N-bromo amine reduced resulted in the near stoichiometric formation of a stable C-Br bond. Collectively, these results demonstrate that N-bromo amines readily promote tyrosine ring-bromination. They also suggest that the scavenging of EPO-generated HOBr/OBr$^-$-by primary amines, abundant moieties in biological fluids, serves as a mechanism for trapping and "funneling" reactive halogen to stable ring-brominated forms of tyrosine.

Eosinophil Peroxidase Generates Stable Ring-brominated Tyrosine Species at Plasma Levels of Halides in High Yield.

The ability of isolated EPO and MPO to form 3-bromotyrosine and 3,5-dibromotyrosine in the presence of physiological levels of halides was evaluated. The results demonstrated that EPO efficiently catalyzed formation of the ring-brominated forms of L-tyrosine even in the presence of a vast molar excess of Cl. Inclusion of a molar excess of taurine in reaction mixtures augmented ring-bromination by EPO, consistent with N-bromo amines as intermediates in the reaction. In contrast, MPO failed to generate significant levels of ring-brominated tyrosine species at physiological levels of halides, even in the presence of excess amines.

Eosinophil Peroxidase Brominates Protein Tyrosine Residues in High Yield at Plasma Levels of Halides.

The ability of isolated EPO to generate 3-bromotyrosine and 3,5-dibromotyrosine on intact proteins was studied. Bovine serum albumin (BSA) was incubated with either EPO or MPO, H$_2$O$_2$, plasma levels of Cl$^-$ (100 mM) and varying levels of Br$^-$ (0–200 mM), and then the content of ring-brominated tyrosine residues formed determined as described. At all concentrations of Br$^-$ examined, EPO promoted bromination of protein tyrosyl residues. In contrast, little if any detectable brominated tyrosine species were formed by isolated MPO. In parallel experiments, BSA was incubated with either EPO or MPO, plasma levels of halides and low doses of H$_2$O$_2$ (0–50 μM). Again, EPO promoted protein tyrosyl residue bromination, but MPO failed to generate any significant brominated products. Examination of the overall yield of the reaction confirmed that EPO—but not MPO—efficiently incorporated halogen into stable ring-brominated forms (C—Br bonds) at plasma levels of halides. Collectively, these results demonstrate that 3-bromotyrosine and 3,5dibromotyrosine are excellent candidate molecular markers for identifying sights of EPO-catalyzed protein oxidative damage in vivo.

Activation of Eosinophils Brominate Protein Tyrosyl Residues Through the EPO-H$_2$O$_2$—Br$^-$ System.

A dramatic increase in 3-bromotyrosine content was observed when BSA was incubated with activated phagocytes. Formation of 3-bromotyrosine required activation of the cells with phorbol ester and the presence of plasma levels of bromide. Addition of peroxidase inhibitors (e.g. NaN$_3$) and a peroxide scavenger (catalase) inhibited 3-bromotyrosine production. In contrast, addition of heat killed catalase (hk catalase) failed to block 3-bromotyrosine formation. Collectively, these results implicate the eosinophil peroxidase-H$_2$O$_2$—Br$^-$ system in the bromination of protein tyrosyl residues.

3-Bromotyrosine is a Specific Marker for Protein Oxidation Mediated by Phagocyte-generated Reactive Brominating Species The ability of human eosinophils and human neutrophils to brominate protein tyrosyl residues and to form 3-chlorotyrosine was examined as a function of bromide concentrations. In the absence of added bromide, neither eosinophils nor neutrophils generated significant amounts of protein-bound 3-bromotyrosine as monitored by stable isotope dilution GC/MS. A dramatic increase in 3-bromotyrosine content was apparent in BSA incubated with activated eosinophils and physiological levels of bromide (5–100 μM). Parallel incubations with activated neutrophils demonstrated only modest increases in 3-bromotyrosine formation, and only at higher levels of bromide. No detectable 3-chlorotyrosine was formed during incubations with eosinophils under all conditions, and 3-chlorotyrosine was formed by neutrophils at all concentrations of Br– examined. These results are consistent with eosinophil peroxidase having a substrate preference for bromide, and myeloperoxidase preferentially utilizing chloride as substrate. Collectively, these results demonstrate that 3-bromotyrosine is selectively formed by eosinophils at physiological levels of bromide.

The following examples are for purposes of illustration only and are not intended to limit the scope of the claims which are appended hereto.

EXAMPLES

Example 1
Measuring Levels of 3-Bromotyrosine in Bronchoalveolar Lavaze of Asthmatic Subjects.

Human bronchoalveolar lavage (BAL) was obtained from ventilated patients admitted to an intensive care unit. Samples from patients admitted to the intensive care unit because of a severe asthma exacerbation were identified and compared to a similar size pool of samples from patient admitted to the intensive care unit for other causes (e.g. head trauma, gun shot wound, post operatively). Samples were immediately placed in ice-cold antioxidant buffer (50 mM phosphate buffer, pH 7.0, supplemented with 100 $\mu$M diethylenetriamine pentaacetic acid, and 100 $\mu$M butylated hydroxytoluene and frozen at −80° C. until analysis. Samples were thawed, delipidated and desalted by vortexing with a single phase extraction mixture comprised of $H_2O$:methanol:$H_2O$-saturated diethyl ether (1:3:7,v:v:v) for 5 min, followed by sitting at 0° C. for 30 min. A protein pellet was recovered following centrifugation at 3000×g (0° C.). $^{13}C_6$-labeled 3-bromotyrosine and $^{13}C_6$-labeled tyrosine were added, the samples dried in a rotary vacuum device, and then subjected to acid hydrolysis with 4 N methane sulfonic acid (0.5 ml) supplemented with 1% phenol for 24 h at 100° C. The standards were prepared by addition of HOBr to $^{13}C_6$-labeled tyrosine in sodium phosphate buffer (50 mM, pH 7.0) and isolated by reverse phase HPLC as described above. Prior to initiating hydrolysis, acid mixtures were degassed under vacuum and then sealed under a blanket of argon.

Following hydrolysis, 1.5 ml of 0.1% trifluoroacetic acid (TFA) was added to the hydrolysate and the mixture passed over a solid phase C18 extraction column (Supelclean LC-18 SPE tubes, from Supelco Inc., Bellefonte, Pa) equilibrated with 0.1% TFA in water. The column was washed with 2 ml of the same buffer, eluted with 2 ml of 20% methanol in 0.1% TFA in water, and the recovered amino acids dried under vacuum.

L-Tyrosine and 3-bromotyrosine were converted to their n-propyl, per heptafluorobutyryl (HFB) derivatives as described in Knapp, D. R. 1979. In Handbook of analytical derivatization reactions. John Wiley and Sons, New York, N.Y., 485–486. 3-Bromotyrosine and tyrosine were quantified by stable isotope dilution GC/MS in the negative-ion chemical ionization mode and analyzed on a Perkin Elmer TurboMass mass spectrometer equipped with chemical ionization probe. Chromatographic separations were performed on a 20 m PE—5MS column (0.18 mm i.d., 0.18 $\mu$m film; Perkin Elmer), and mass spectra were acquired in the negative-ion mode. The column was run with the following temperature gradient: 150° C. to 250° C. at 20° C./min. The injector, transfer line and source temperatures were set at 250° C., 250° C. and 130° C., respectively. 3-Bromotyrosine was monitored as its n-propyl per HFB derivative using two structurally informative fragment ions, m/z 573 (M—HF)$^-$ and m/z 445 (M—$CF_3CF_2CHO$)$^-$ and their corresponding isotopically labeled [$^{13}C_6$] internal standard ions at m/z 579 and 451, respectively. L-Tyrosine was monitored as its n-propyl-per-HFB derivative using the base peak at m/z 417 ($M^{\bullet-}$—HFB), another major ion at m/z 595 ($M^{\bullet-}$—HF), and their corresponding isotopically labeled internal standard ions at m/z 423 and 601, respectively. The ratio of ion currents of the two characteristic ions of each compound and its corresponding internal standard were monitored in all analyses to ensure that interfering ions were not co-eluting with the analyte. The limit of detection (S/N$\geq$4) for 3-bromotyrosine by this technique is less than 10 fmol on column.

Figure 4:
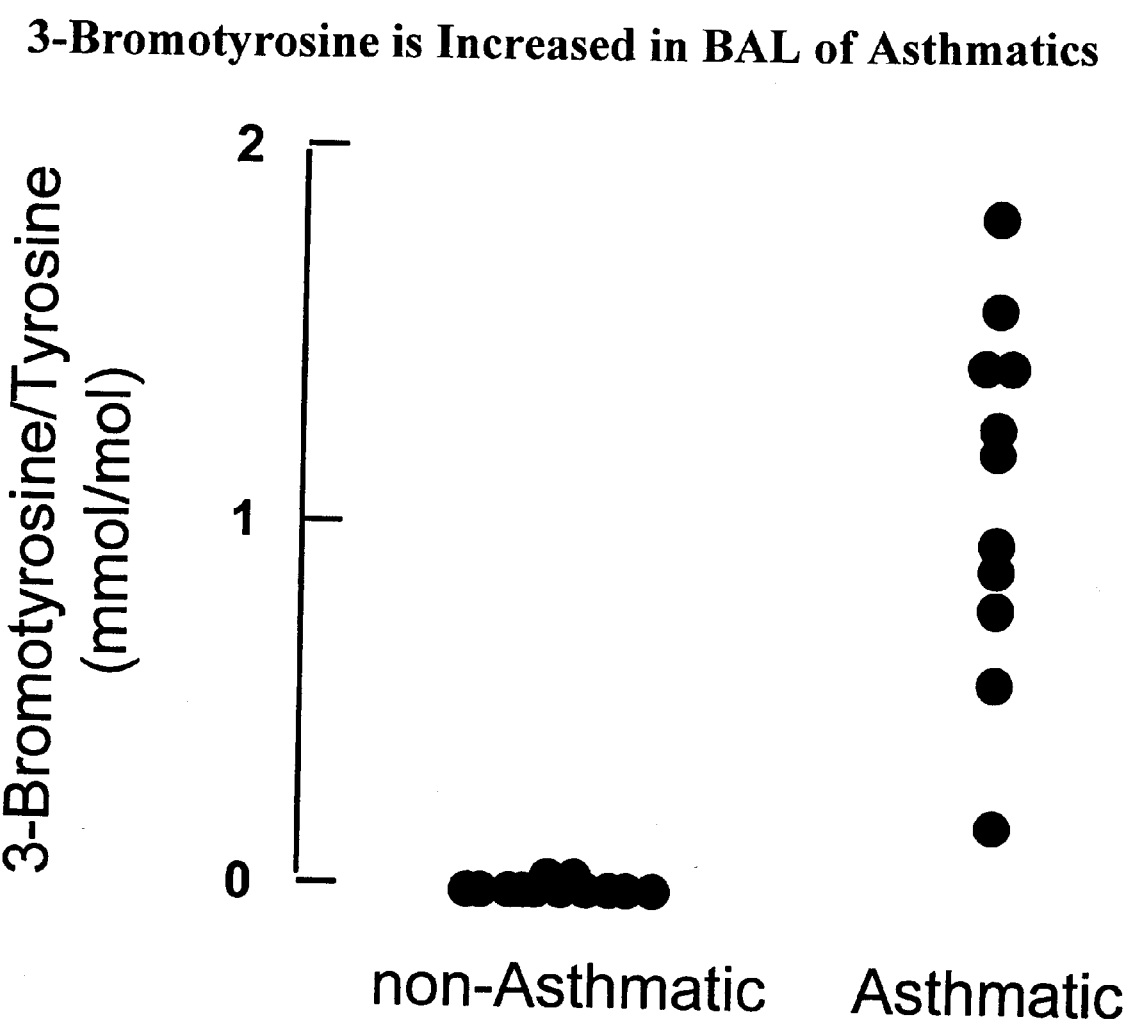
FIG. 4 is a graph showing 3-bromotyrosine content in bronchoalveolar lavage obtained from asthmatic and non-asthmatic subjects

Results represented as the mean±SEM are shown in FIG. 4. Mass spectrometric analysis revealed levels of 3-bromotyrosine in BAL of asthmatic subjects that were over 100-fold higher than those of non-asthmatic individuals 3-Bromotyrosine was barely detectable in BAL from non-asthmatics. Thus, 3-bromotyrosine is a useful diagnostic marker for asthma.

Example 2
Measuring Levels of 3-Bromotyrosine in Bronchoalveolar Lavage of Asthmatic Subjects Following Segmental Antigen Challenge Normal saline containing ragweed pollen was infused into to a specific lung segment of at least 6 subjects known to have asthma (test subjects) and to a specific lung segment of at least 6 control subjects. A control normal saline solution lacking antigen was administered to the contralateral lung at a different and separate specific lung segment of each test subject and each control subject. After 48 h, subjects again underwent bronchoscopy and the antigen challenged segment and normal saline challenged segment of each test subject and each control subject was lavaged with normal saline. Broncho-alveolar fluids recovered were analyzed as described above in Example 1 and the content of 3-bromotyrosine and 3-chlorotyrosine in the fluids determined.

Figure 5:
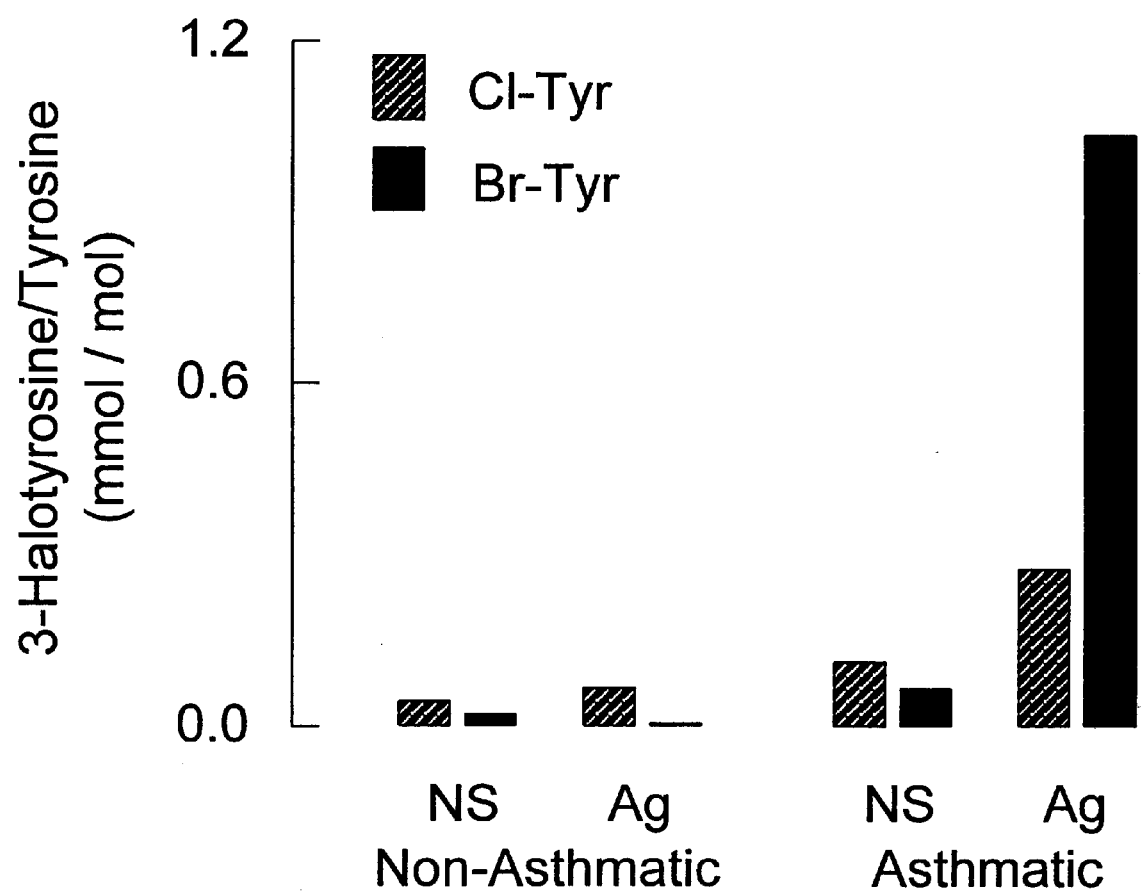
FIG. 5 is a graph showing 3-bromotyrosine content in bronchoalveolar lavage obtained from mild. asthmatic subjects following exposure to an allergen.

As shown in FIG. 5, a 2-fold increase in the baseline levels of 3-bromotyrosine were observed in the mild (none required continuous oral or metered dose inhaler steroid therapy) asthmatic subjects that were tested. Furthermore, following exposure to the antigen challenge, the level of 3-bromotyrosine in asthmatic individuals increased significantly, but no increase was observed in similarly exposed non-asthmatic subjects. Furthermore, 3-chlorotyrosine levels increased much less than 3-bromotyrosine levels in response to antigen challenge in both asthmatic and non-asthmatic subjects. 3-Chlorotyrosine is a specific marker for myeloperoxidase-dependent tissue injury from other inflammatory cells including neutrophils, monocytes and tissue macrophages.

These results demonstrate that the present method is useful for identifying low levels of eosinophil inflammatory injury, even in mild asymptomatic asthmatics, since baseline levels of 3-bromotyrosine were significantly increased in the asthmatic subjects as compared to the non-asthmatic subjects. They also demonstrate that 3-bromotyrosine is selectively formed in asthmatic subjects following exposure to an allergen. They also demonstrate that 3-bromotyrosine is a specific and superior index of tissue injury in asthmatics exposed to an allergen challenge because much smaller increases were noted in the content of 3-chlorotyrosine in asthmatic vs. non-asthmatic lavage fluids

Example 3
Measuring Plasma Levels of 3-Bromotyrosine in a Subject with an Acute Asthma Exacerbation and Following Initiation of Steroid Therapy.

A 23 year old male with 15 year history of asthma notable for 2 prior hospitalizations (last one 2 years ago) was admitted to the hospital for a severe asthma exacerbation not responsive to therapy in the Emergency Department. The subject had required multiple courses of oral steroid therapy in the past for worsening of asthma symptoms, but no oral steroids had been required for the months preceding the current hospitalization. The subject's asthma was being treated with albuteral metered dose inhaler taken as needed. No predisposing respiratory infection was noted. Blood samples were taken upon admittance to the Emergency Department, and then at multiple successive time intervals following treatment with intravenous (i.v.) and then oral steroids on a tapering dose over the course of the next 2 weeks. Blood was collected into EDTA chelated tubes and then spun at 4000×g to pellet and remove cells. Plasma was supplemented with antioxidant buffer and stored frozen at −80° C. until analysis as in Example 1. The content of 3-bromotyrosine was determined by stable isotope dilution GC/MS as described in Example 1.

Figure 6:
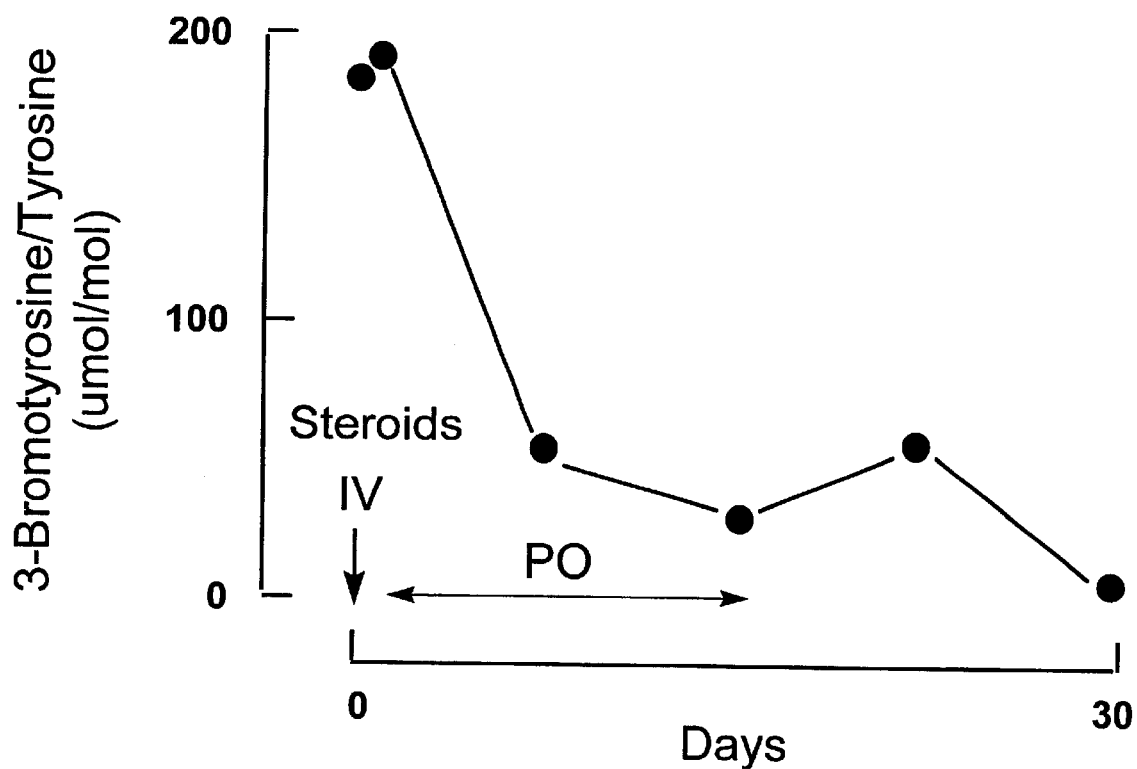
FIG. 6 is a graph showing 3-bromotyrosine content in plasma of an asthmatic subject following admission to the hospital for acute asthma exacerbation and following intravenous and oral steroid therapy.

As shown in FIG. 6, the content of 3-bromotyrosine in plasma proteins at day 0 was greater than 200 μmol/mol protein tyrosine However, the content of 3-bromotyrosine in plasma decreased significantly following steroid therapy. The subject experienced marked symptomatic improvement within the first 24 h of treatment, with symptoms disappearing almost entirely to his background level of intermittent cough with heavy exertion by 2 weeks after admission. These results demonstrate that the present diagnostic method is useful for monitoring the efficacy of anti-asthmatic therapies in subjects with asthma.

Example 4
Measuring Levels of 3-Bromotyrosine in Tissue Samples from Subjects Challenged with a Food Allergen Several days following exposure to either control diet (NS) (4 mice) or diet containing egg white protein to which the mice were allergic (e.g. ovalbumin, Ova) (4 mice), the small bowel of the mice was excised and placed in buffer containing an antioxidant cocktail and the frozen at −80° C. until analysis as described in Example 1. Tissues were thawed, homogenized, delipidated and desalted, hydrolyzed and then the levels of 3-bromotyrosine determined by stable isotope dilution GC/MS as described in Example 1.

Figure 7:
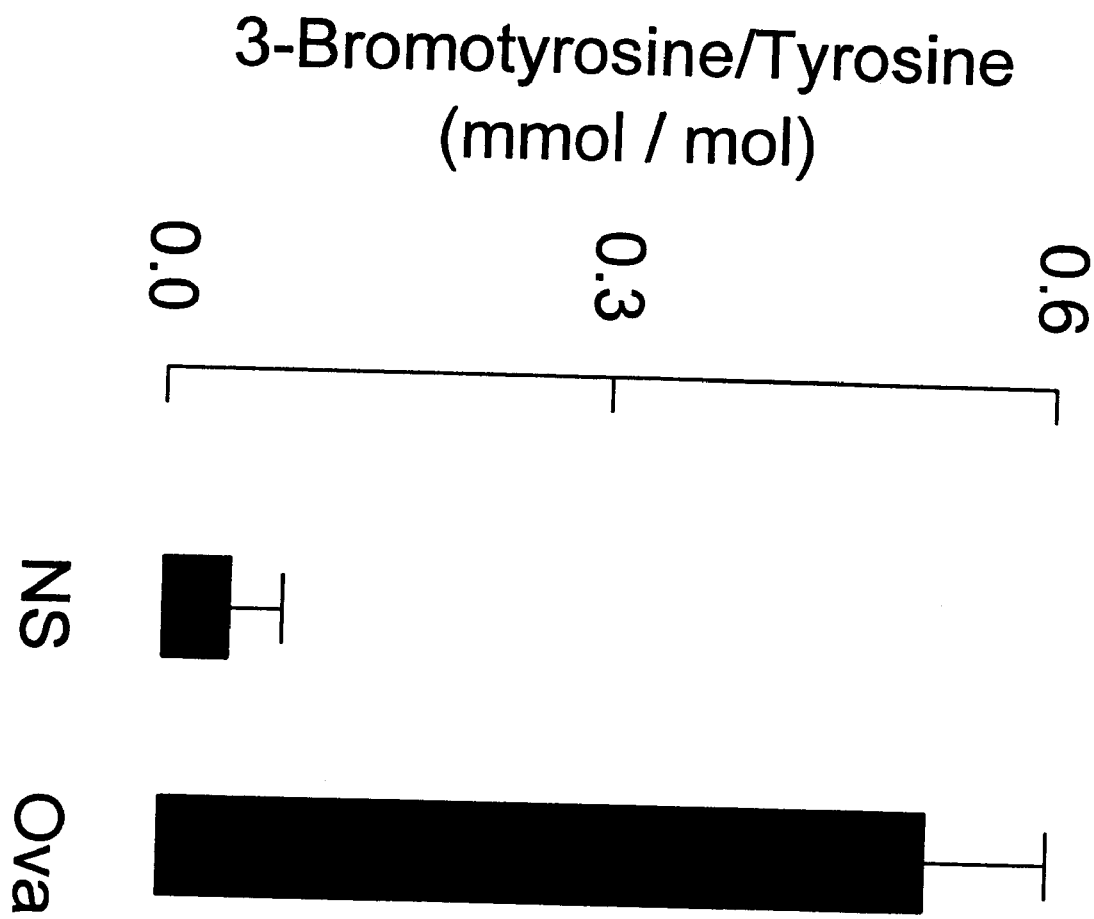
FIG. 7 is a graph showing 3-bromotyrosine content in the small bowel of mice exposed to a food allergen.

As shown in FIG. 7, 3 bromotyrosine levels were much greater in bowel segments obtained from mice that had been fed diets containing food to which they were allergic, as compared to controls. Thus, the present diagnostic method is useful for diagnosing diseases, such as for example, food allergy, inflammatory bowel disease, and other analogous diseases which are associated with eosinophilic infiltration.

Example 5
Detecting the Presence of 3-Bromotyrosine in Urine from an Asthmatic Subject Urine (20 cc) from an asthmatic individual who sought treatment at the Emergency Department because of a severe asthma exacerbation, and a corresponding volume of urine from a non-asthmatic healthy individual were analyzed for the presence of free 3-bromotyrosine by HPLC with electrospray mass spectrometry. Electrospray ionization mass spectrometry (ESI/MS) was performed on a Quatro II Triple Quadruple Mass Spectrometer (Micromass, Inc.) interfaced with an HP 1100 HPLC (Hewlett Packard). 3-Bromotyrosine was resolved on a C18 column (5 μm, 1.0×150 mm) at a flow rate of 30 μl/min and a linear gradient between $H_2O$ (+0.3% formic acid) and methanol (+0.3% formic acid) over 20 min. Column eluent was analyzed by the mass spectrometer in the positive-ion mode with a cone potential of 23 eV. 3-Bromotyrosine was monitored in selected ion monitoring mode at mass to charge ratio 260. Peak identity was confirmed by demonstrating comigration of both the $^{79}Br$ (m/z 260) and $^{81}Br$ (m/z 262) isotopomers (at 1:1 relative integrated areas) at the retention time of authentic 3-bromotyrosine. 3-Bromotyrosine was only observed in the urine of the asthmatic individual.

Figure 8:
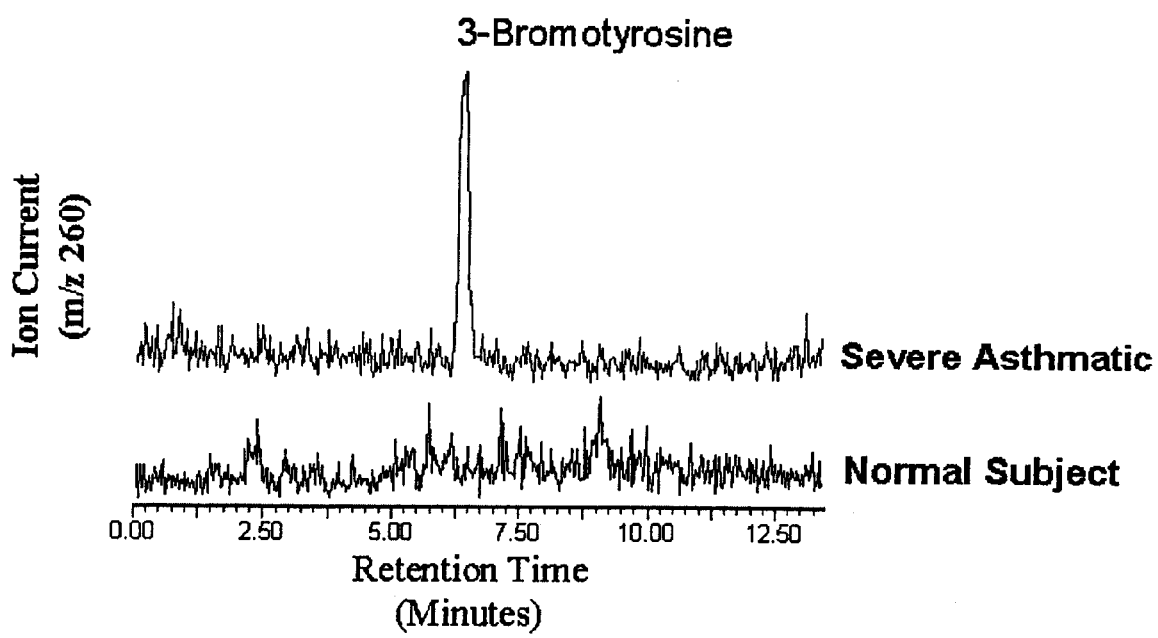
FIG. 8 is a graph showing the presence of 3-bromotyrosine in urine from an asthmatic subject, and the lack of detectable 3-bromotyrosine in the urine of a normal subject.

As shown in FIG. 8, 3-bromotyrosine is present in the urine of an asthmatic subject. The marker is not observed in urine from a normal individual. Thus, urinary levels of 3-bromotyrosine may be monitored to serve as a non-invasive indicator of the extent of protein damage by brominating oxidants, such as in eosinophil-dependent inflammatory tissue injury in an asthmatic, or for the diagnosis of asthma or a similar disorder in individuals.

What is claimed is:

1. A method for diagnosing a disease associated with activated eosinophils in a subject comprising:
    assaying for the presence of elevated levels of a brominated tyrosine species in a test sample of a body fluid or tissue obtained from the subject,
    wherein the brominated tyrosine species is selected from the group consisting of 3-bromotyrosine, 3,5-dibromotyrosine, and combinations thereof, and
    wherein the presence of elevated levels of said brominated tyrosine species in the sample correlates with the presence of said disease in the subject.

2. The method of claim 1 in which the test sample is selected from the group consisting of bronchoalveolar lavage, serum, plasma, urine, tissue biopsy, sputum, induced sputum, blood, pericardial fluid, pleural fluid, cerebrospinal fluid, stool, and broncho-alveolar lavage cells containing metabolic products of activated eosinophils and phagocytes.

3. A method of diagnosing asthma in a subject suspected of having asthma comprising:
    assaying for the presence of elevated levels of a brominated tyrosine species in a test sample of a body fluid or tissue obtained from the subject,
    wherein the brominated tyrosine species is selected from the group consisting of 3-bromotyrosine, 3,5-dibromotyrosine, and combinations thereof, and
    wherein the presence of elevated levels of said brominated tyrosine species in the sample correlates with the presence of asthma in the subject.

4. The method of claim 3 wherein the assay comprises determining the concentration or content of the brominated tyrosine species in the test sample.

5. The method of claim 4 further comprising the step of comparing the concentration or content of the brominated species in the test sample to the concentration or content of the brominated species in corresponding samples from normal subjects lacking asthma.

6. The method of claim 3 wherein the concentration or content of the brominated species in the test sample is compared to a baseline concentration or content of the brominated species in a corresponding sample from the test subject.

7. The method of claim 3 wherein the assay comprises determining the concentration or content of the brominated species in a plurality of test samples obtained at successive time intervals from the subject.

8. The method of claim 3 wherein the assay comprises determining the concentration or content of the brominated species in a test sample obtained from the subject at a time prior to treatment with an anti-asthmatic drug and determining the concentration or content of the brominated species in a corresponding test sample obtained from the subject at a time following treatment with an anti-asthmatic agent.

9. The method of claim 1 wherein the presence of elevated levels of the brominated tyrosine species in the test sample is assayed by a technique selected from mass spectrometric analysis, HPLC with electrochemical detection, HPLC with fluorescence detection following pre- or post column derivatization, Capillary Electrophoresis, and high resolution NMR spectroscopy.

10. The method of claim 1 wherein the presence of elevated levels of the brominated tyrosine species in the sample is assayed by contacting the sample with an anti-bromotyrosine monoclonal antibody and assaying for the formation of an antigen-antibody complex between said antibody and a protein in said sample, wherein said protein contains a bromotyrosine.

11. A diagnostic kit for diagnosing diseases in which activated eosinophils are present at the discase site, said kit comprising an antibody that specifically reacts with a brominated tyrosine species, wherein the brominated tyrosine species is contained within a peptide or protein.

12. The diagnostic kit of claim 11 wherein said antibody is a monoclonal antibody and said brominated tyrosine species is selected from the group consisting of 3-bromotyrosine, 3,5-di-bromotyrosinc, and combinations thereof.

13. The diagnostic kit of claim 12 further comprising a synthetic peptide or a synthetic protein containing bromotyrosine.

14. The method of claim 1 in which the presence of elevated levels of the brominated tyrosine species is detected by an immunoassay which employs antibodies to 3-bromotyrosine, or to 3,5di-bromotyrosine, or to 3-bromotyrosine and 3,5-dibromotyrosine.

15. The method of claim 1 wherein the disease is associated with the presence of increased concentrations of 3-bromotyrosine or 3,5-dibromotryosine in samples from subjects having the disease relative to samples from normal subjects lacking the disease.

16. The method of claim 3 further comprising the steps of measuring the amount of a reference compound in the sample and normalizing the amount of the brominated tyrosine species to the amount of the reference compound.

17. The method of claim 16 wherein said reference compound is an index of total protein content.

18. The method of claim 16 wherein said reference compound is selected from the group consisting of an amino acid, total protein content, albumin, creatinine, and combinations thereof.

19. The method of claim 4 further comprising the steps of determining the concentration or the content of a reference compound in the sample and normalizing the concentration or content of the brominated tyrosine species to the concentration or content of the reference compound.

20. The method of claim 19 wherein said reference compound is an index of total protein content.

21. The method of claim 19 wherein said reference compound is selected from the group consisting of an amino acid, total protein content, albumin, creatinine, and combinations thereof.

22. The method of claim 3 wherein the test sample is selected from the group consisting of serum, plasma, urine, tissue biopsy, sputum, induced sputum, fluid or cells contained in a broncheoalveolar lavage, and blood.

23. The method of claim 3 wherein the presence of elevated levels of the brominated species in the test sample is assayed by a technique selected from mass spectrometric analysis, HPLC with electrochemical detection, HPLC with fluorescence detection following pre- or post column derivatization, Capillary Electrophoresis, and high resolution NMR spectroscopy.

24. The method of claim 3 wherein the presence of elevated levels of the brominated species in the sample is assayed by contacting the sample with an anti-bromotyrosine monoclonal antibody and assaying for the formation of an antigen-antibody complex between said antibody and a protein or peptide in said sample, wherein said protein or peptide contains a bromotyrosine.

25. The method of claim 1 further comprising the steps of determining the concentration or the content of a reference compound in the sample and normalizing the concentration or content of the brominated tyrosine species to the concentration or content of the reference compound.

26. The method of claim 25 wherein said reference compound is an index of total protein content.

27. The method of claim 25 wherein said reference compound is selected from the group consisting of an amino acid, total protein content, albumin, creatinine, and combinations thereof.

28. A method of diagnosing an allergy in a subject suspected of having an allergy comprising:
assaying for the presence of elevated levels of a brominated tyrosine species in a test sample of a body fluid or tissue obtained from the subject,
wherein the brominated tyrosine species is selected from the group consisting of 3-bromotyrosine, 3,5-dibromotyrosine, and combinations thereof, and
wherein the presence of elevated levels of said brominated tyrosine species in the sample correlates with the presence of an allergy in said subject.

29. The method of claim 28 in which the test sample is selected from the group consisting of serum, plasma, urine, tissue biopsy, sputum, blood, and stool.

30. The method of claim 28 wherein the presence of elevated levels of the brominated species in the test sample is assayed by a technique selected from mass spectrometric analysis, HPLC with electrochemical detection, HPLC with fluorescence detection following pre- or post column derivatization, Capillary Electrophoresis, and high resolution NMR spectroscopy.

31. The method of claim 28 wherein the presence elevated levels of the brominated species in the sample is assayed by contacting the sample with an anti-bromotyrosine monoclonal antibody and assaying for the formation of an antigen-antibody complex between said antibody and a protein or peptide in said sample, wherein said protein or peptide contains a bromotyrosine.

32. The method of claim 28 in which the presence of elevated levels of the brominated tyrosine species is detected by an immunoassay which employs antibodies to 3-bromotyrosine, or 3,5di-bromotyrosine, or to 3-bromotyrosine and 3,5-dibromotyrosine.

33. The method of claim 28 wherein the allergy is associated with the presence of increased concentrations of 3-bromotyrosine or 3,5-dibromotyrosine in samples from subjects having the allergy relative to samples from normal subjects.

34. The method of claim 28 further comprsing the steps of determining the concentration or the content of a reference compound in the sample and normalizing the concentration or content of the brominated tyrosine species to the concentration or content of the reference compound.

35. The method of claim 34 wherein said reference compound is an index of total protein content.

36. The method of claim 34 wherein said reference compound is selected from the group consisting of an amino acid, total protein content, albumin, creatinine, and combinations thereof.

37. A method of diagnosing a disease associated with inflammation and activated eosinophils in a subject comprising:
assaying for the presence of elevated levels of a brominated tyrosine species in a test sample of a body fluid or tissue obtained from the subject,
wherein said brominated tryrosine species is wherein the brominated tyrosine species is selected from the group consisting of 3-bromotyrosine, 3,5-dibromotyrosine, and combinations thereof, and wherein the presence of elevated levels of said brominated tyrosine species in the sample is correlated with the presence of said disease in the subject.

38. The method of claim 37 wherein the test sample is selected from the group consisting of serum, plasma, urine, tissue biopsy, sputum, induced sputum, fluid or cells contained in a broncheoalveolar lavage, and blood.

39. The method of claim 37 wherein the presence of elevated levels of the brominated species in the test sample is assayed by a technique selected from mass spectrometric analysis, HPLC with electrochemical detection, HPLC with fluorescence detection following pre- or post column derivatization, Capillary Electrophoresis, and high resolution NMR spectroscopy.

40. The method of claim 37 wherein the presence of elevated levels of the brominated species in the sample is assayed by contacting the sample with an anti-bromotyrosine monoclonal antibody and assaying for the formation of an antigen-antibody complex between said antibody and a protein or peptide in said sample, wherein said protein or peptide contains a bromotyrosine.

41. The method of claim 37 in which the presence of elevated levels of the brominated tyrosine species is detected by an immunoassay which employs antibodies to 3-bromotyrosine, or to 3,5di-bromotyrosine, or to 3-bromotyrosine and 3,5-dibromotyrosine.

42. A diagnostic kit for diagnosing diseases in which activated eosinophils are present at the disease site, said kit comprising an antibody that specifically reacts with 3-bromotyrosine, or 3'5 di-bromotyrosine, or 3-bromotyrosine and a 3,5dibromotyrosine, wherein the bromotyrosine is either free or contained within a peptide or protein.

43. The diagnostic kit of claim 42 wherein said antibody is a monoclonal antibody.

* * * * *

UNITED STATES PATENT AND TRADEMARK OFFICE
CERTIFICATE OF CORRECTION

PATENT NO.         : 6,306,576 B1                                      Page 1 of 1
APPLICATION NO. : 09/253380
DATED              : October 23, 2001
INVENTOR(S)        : Stan Hazen et al.

It is certified that error appears in the above-identified patent and that said Letters Patent is hereby corrected as shown below:

Col. 1, after the title and before the BACKGROUND OF THE INVENTION section, please insert the following paragraph:

--This invention was made at least in part with government suport under R01-HL061878-01 awarded by the National Institutes of Health. The U.S. government has certain rights in the invention.--

Signed and Sealed this

Seventeenth Day of July, 2007

JON W. DUDAS
*Director of the United States Patent and Trademark Office*